(12) United States Patent
Azimi et al.

(10) Patent No.: US 10,178,963 B1
(45) Date of Patent: Jan. 15, 2019

(54) GAS COLLECTION APPARATUS AND METHOD TO ANALYZE A HUMAN BREATH SAMPLE

(71) Applicants: Saeed Azimi, Los Gatos, CA (US); Elaheh Farjami, San Jose, CA (US)

(72) Inventors: Saeed Azimi, Los Gatos, CA (US); Elaheh Farjami, San Jose, CA (US)

(73) Assignee: DYNOSENSE, CORP., Wilmington, DE (US)

( * ) Notice: Subject to any disclaimer, the term of this patent is extended or adjusted under 35 U.S.C. 154(b) by 280 days.

(21) Appl. No.: 15/178,407

(22) Filed: Jun. 9, 2016

(51) Int. Cl.
| *A61B 5/00* | (2006.01) |
| *A61B 5/097* | (2006.01) |
| *A61B 5/08* | (2006.01) |
| *G01N 33/497* | (2006.01) |

(52) U.S. Cl.
CPC .............. *A61B 5/097* (2013.01); *A61B 5/082* (2013.01); *A61B 5/7282* (2013.01); *G01N 33/497* (2013.01)

(58) Field of Classification Search
None
See application file for complete search history.

(56) References Cited

U.S. PATENT DOCUMENTS

| 9,945,878 | B1 * | 4/2018 | Gordon | G01N 33/948 |
| 2003/0050567 | A1 * | 3/2003 | Baghdassarian | A61B 5/0836 600/532 |
| 2004/0210154 | A1 * | 10/2004 | Kline | A61B 5/417 600/532 |
| 2005/0161042 | A1 * | 7/2005 | Fudge | A61B 5/097 128/205.12 |
| 2009/0187111 | A1 * | 7/2009 | Reilly, Jr. | A61B 5/097 600/532 |
| 2015/0105683 | A1 * | 4/2015 | Bos | A61B 5/082 600/532 |

* cited by examiner

*Primary Examiner* — Tiffany Weston
*Assistant Examiner* — Sarah R Kingsley
(74) *Attorney, Agent, or Firm* — Plager Schack LLP; Mark H. Plager; Eric Liou

(57) ABSTRACT

A gas collection apparatus for use by a user includes a housing with an inlet and an outlet to permit a breath sample to flow therethrough. The housing includes a first compartment and a second compartment, a chemo-resistive analysis assembly having a substrate coupled to a sensor array and disposed within the first compartment, the substrate being operably connected to a voltage control unit coupled to the housing to heat the sensor array to a desired temperature, a resistance control unit coupled to the housing to measure resistance in the sensor array, an optical analysis assembly having a light-emitting diode array and a photodiode array coupled to the second compartment, and a processor coupled to the housing and operably connected to the chemo-resistive analysis and optical analysis assemblies.

7 Claims, 4 Drawing Sheets

GAS COLLECTION APPARATUS AND METHOD TO ANALYZE A HUMAN BREATH SAMPLE

BACKGROUND

The embodiments herein relate generally to an apparatus and method for analyzing a human's breath.

The human breath is complex and is estimated to have as many as 200 different gas components in a typical sample. Some of these gases are present in small quantities such as 1-100 parts per billion (ppb), which presents a need for accurate methods and devices to properly detect these components.

Several optical and chemo-resistive analyses have been used to determine the ratio of gases present in a sample. Optical analyses are conducted through the use of sensors known as opto-sensors. Gases in a sample are exposed to a light generated by a source. The interaction of the gases with the light causes the intensity and/or wavelength of light to change. By analyzing the change in wavelength of the light, the ratio of gases present in a sample can be estimated.

Chemo-resistive analyses are conducted through the use of sensors known as chemo-sensors or electro chemo-resistive material. During these analyses, gases in a sample interact with the sensors, which causes the resistance properties of the sensors to change. The sensing material of the chemo-sensors are generally heated to a high temperature within the range of 50-700 degrees Celsius. This heating process increases the selectivity and sensitivity of the chemo-sensors to the present gases. For example, a chemo-sensor's resistance can change dramatically in the presence of oxygen when heated to 400 degrees Celsius, but not very much at other temperatures. The same chemo-sensor's resistance might change dramatically in the presence of acetone when heated to 600 degrees Celsius. By measuring the resistances of one or more chemo-sensors at various temperatures, the ratio of gases present in a sample can be estimated.

Although there are numerous studies on the development of optical and chemo-resistive techniques and devices, the development of portable devices with the capability of detecting trace amounts of gases in a sample remain a challenge.

As such, there is a need in the industry for a gas collection apparatus and method for determining the ratio of gases in a sample with enhanced accuracy. Specifically, there is a need for a gas collection apparatus and method that combines both optical and chemo-resistive analyses to determine the ratio of gases present in a human's breath sample.

SUMMARY

A gas collection apparatus for use by a user to perform an optical and chemo-resistive analyses on a breath sample to identify any one of a plurality of conditions suffered by the user is provided. The gas analysis apparatus comprises a housing comprising a sealable inlet and a sealable outlet configured to permit the breath sample to flow therethrough, the housing comprising a first compartment and a second compartment, a chemo-resistive analysis assembly comprising a substrate with heating elements coupled to a sensor array and disposed within the first compartment, the heating elements of the substrate being operably connected to a voltage control unit coupled to the housing and configured to heat the sensor array to a desired temperature, and a resistance control unit coupled to the housing and configured to measure resistance in the sensor array, an optical analysis assembly comprising a light-emitting diode array and a photodiode array coupled to opposing walls of the second compartment, and a processor coupled to the housing and operably connected to the chemo-resistive analysis and optical analysis assemblies, wherein the processor is configured to determine a first ratio of gases present in the breath sample based on the measured resistance in the sensor array upon an interaction with the breath sample in the first compartment, wherein the processor is configured to determine a second ratio of gases present in the breath sample based on a change of intensity and/or wavelength of light emitted by the light-emitting diode array as determined by the photodiode array upon an interaction with the breath sample in the second compartment.

In certain embodiments, a method for performing an optical and chemo-resistive analyses on a breath sample of a user to identify any one of a plurality of conditions suffered by the user is provided. The method comprises providing the gas collection apparatus, collecting the breath sample within the housing to fill the first and second compartments, determining a ratio of gases in the breath sample based on the measured resistance in the sensor array upon an interaction with the breath sample in the first compartment and a change of intensity and/or wavelength of light emitted by the light-emitting diode array as determined by the photodiode array upon an interaction with the breath sample in the second compartment, and identifying any of the one of a plurality of conditions suffered by the user based on the ratio of gases in the breath sample.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
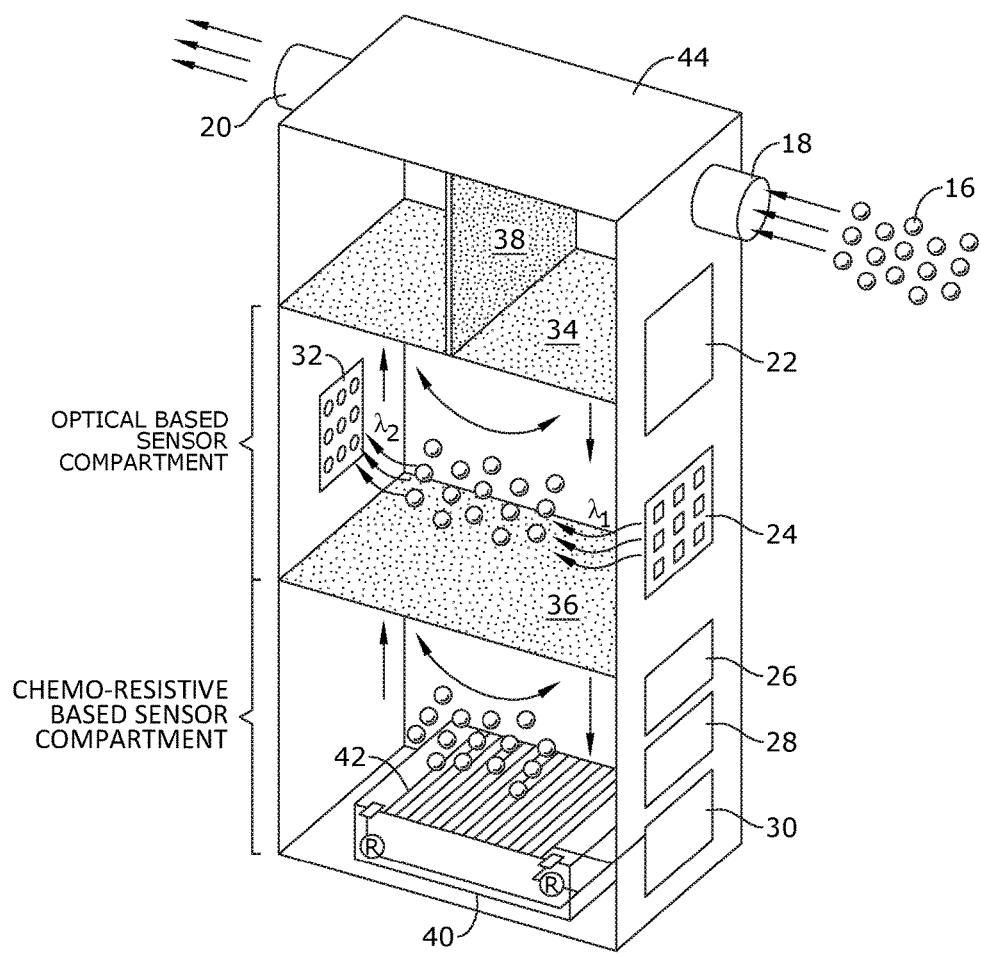
FIG. 1 depicts a schematic view of certain embodiments of the gas collection apparatus.

As depicted in FIG. 1, a gas collection apparatus is configured to collect an analyte such as breath sample 16 and determine the ratio of gases present in the sample with enhanced accuracy. This is useful in identifying and/or monitoring any health conditions or diseases suffered by a user (not shown). The gas collection apparatus generally comprises housing 44, inlet 18, outlet 20, first filter membrane 34, second filter membrane 36, CPU 22, valve control unit 26, voltage control unit 28 and resistance control unit 30.

Housing 44 comprises a plurality of compartments including an optical based sensor compartment and a chemo-resistive based sensor compartment. In the top portion of housing 44, inlet 18 and outlet 20 are coupled to opposing side walls. Inlet 18 comprises an inlet sensor (not shown) disposed therein. In certain embodiments, outlet 20 may comprise an outlet sensor (not shown) disposed therein. Inlet and outlet sensors are operably connected to valve control unit 26 and are configured to detect the pressure of air flowing therethrough. Air pressure data received by valve control unit 26 from inlet and/or outlet sensors are transmitted to CPU 22, which is configured to open and/or close inlet 18 and outlet 20 based on the data. Interior wall 38 is coupled to first filter membrane 34 and the top face of housing 44. This creates two interior channels, a first channel to direct air flowing in via inlet 18 and a second channel to direct air flowing out via outlet 20.

The optical based sensor compartment of housing 44 is created by space between first filter membrane 34, second filter membrane 36 and side walls of housing 44. The optical based sensor compartment is configured to perform an optical analysis of an air and/or breath sample present therein. In the optical based sensor compartment, LED array 24 is coupled to a first side wall and photodiode array 32 is coupled to a second side wall opposite the first side wall. LED array 24 is operably connected to CPU 22 and may comprise any number of light-emitting diodes in various arrangements. The light-emitting diodes in LED array 24 may be configured to emit light having different wavelengths. Photodiode array 32 is operably connected to CPU 22 and is configured to detect the change in intensity and/or wavelength and/or energy of light emitted by LED array 24 after interacting with the air sample present in the compartment.

The chemo-resistive based sensor compartment of housing 44 is created by space between second filter membrane 36, the bottom face of housing 44 and side walls of housing 44. Sensor array 42 and substrate 40 are both disposed within the chemo-resistive based sensor compartment and are operably connected to voltage control unit 28, resistance control unit 30 and CPU 22. Voltage control unit 28 is configured to send voltage to heater elements of substrate 40 to heat sensor array 42 to a desired temperature. Resistance control unit 30 is configured to measure the resistance in sensor array 42 at any given time. CPU 22 controls both voltage control unit 28 and resistance control unit 30, and records any operational data generated by these units.

Substrate 40 is preferably made from glass or other flexible polymer and is configured to house heater elements (not shown) and support sensor array 42. In one embodiment, the heater elements may comprise any micro-heater structures known in the field. Sensor array 42 may include any number and type of materials including, but not limited to, semiconducting oxides such as $WO_3$, $MoO_3$, $SnO_2$, $TiO_2$ and $Sb:SnO_2$, polymers such as polyaniline and polypyrrole, and metal catalysts such as Pd, Pt, Ni, Cu, Ag and Fe. These exemplary sensing materials are used for determining the presence of certain elements in an air or breath sample such as acetone, ethanol, methanol, ammonia, carbon dioxide, nitric oxide, or the like.

Figure 2:
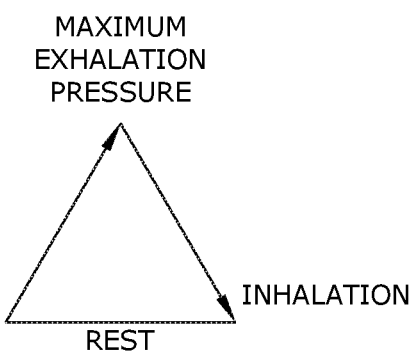
FIG. 2 depicts a schematic view of certain embodiments of the gas collection apparatus.
Figure 3:
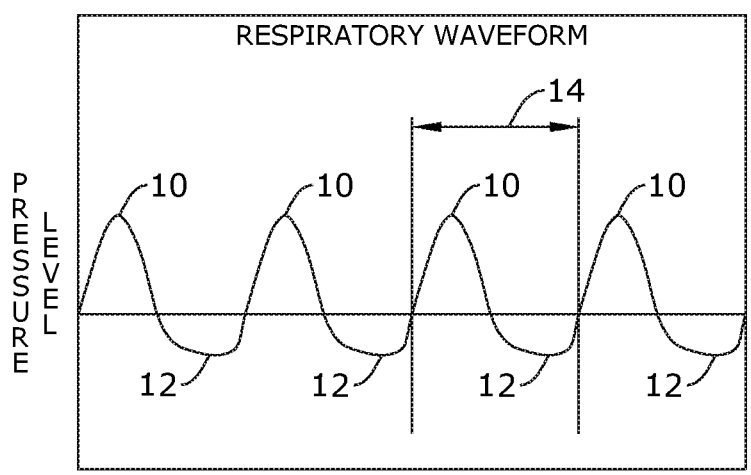
FIG. 3 depicts a schematic view of certain embodiments of the gas collection apparatus.

In operation, the gas collection apparatus is configured to capture and analyze breath sample 16 from a user (not shown). FIGS. 2-3 depict a typical human breath cycle, which comprises three components. The human breath cycle 14 comprises an inhalation period, rest period and exhalation period. These components repeat as the human continues to inhale and exhale. Each breath cycle 14 comprises an exhalation leading to a maximum positive peak pressure 10 and an inhalation leading to a maximum negative peak pressure 12.

In one exemplary embodiment, the user generates breath sample 16 by exhaling through inlet 18 as shown in FIG. 1. CPU 22 detects an exhalation cycle via the inlet sensor. In a preferred embodiment, CPU 22 opens both inlet 18 and outlet 20 when the exhalation reaches maximum positive peak pressure 10. At this time, breath sample 16 flows in housing 44 and is directed downward by interior wall 38. Breath sample 16 flows through first filter membrane 34 to the optical based sensor compartment and through second filter membrane 36 to the chemo-resistive based sensor compartment.

First and second filter membranes 34, 36 are configured to prevent undesirable particulates from reaching the optical based sensor and chemo-resistive based sensor compartments. Undesirable particulates may include, but are not limited to, moisture or dust, which may negatively affect the accuracy of a breath sample analysis. Remaining portions of breath sample 16 continue to flow up through second filter membrane 36, first filter membrane 34 and out of housing 44 via outlet 20. At the end of the exhalation's positive peak pressure, CPU 22 automatically closes inlet 18 and outlet 20. This retains breath sample 16 within housing 44.

Once breath sample 16 is captured, optical and chemo-resistive analyses on breath sample 16 are performed simultaneously. Specifically, CPU 22 enables the optical analysis of breath sample 16 by activating LED array 24. LED array 24 emits light having different wavelengths A. Each gas is sensitive to light of a certain wavelength. In one exemplary configuration, a particular gas will interact with light comprising wavelength $\lambda_1$, absorb energy and change the intensity and/or wavelength of the light to $\lambda_2$. Photodiode array 32 detects the changes in intensity and/or wavelength of all light emitted by LED array 24 after interacting with breath sample 16 in the optical based sensor compartment. From data generated by photodiode array 32, CPU 22 can determine the ratio of gases present in breath sample 16.

CPU 22 enables the chemo-resistive analysis on breath sample 16 by permitting voltage control 28 to transmit voltage to the heating elements (not shown) of substrate 40 to heat sensor array 42 to a desired temperature. This temperature may vary to enhance the sensitivity of one or more sensors in sensor array 42 to certain gases/elements in breath sample 16. Breath sample 16 interacts with all sensors in sensor array 42. This causes the resistance in one or more sensors to change as detected by resistance control unit 30. By analyzing the resistances of one or more sensors in sensor array 42 at various temperatures, CPU 22 can determine the ratio of gases present in breath sample 16.

CPU 22 compares and analyzes data from both the optical and chemo-resistive analyses described above. This enhances the gas collection apparatus' accuracy in determining the ratio of gases present in breath sample 16. An accurate determination of the gases present in a breath sample can help a healthcare professional to identify and/or monitor certain conditions and/or diseases. For example, a diabetic patient will exhale excessive acetone in a breath sample. A patient suffering from asthma will exhale elevated amounts of nitric oxide. It shall be appreciated that the gas collection apparatus may have one or more memory storage units to save data generated from the optical and chemo-resistive analyses. The data may be retrieved easily and/or transmitted to a remote location as needed.

Figure 4:
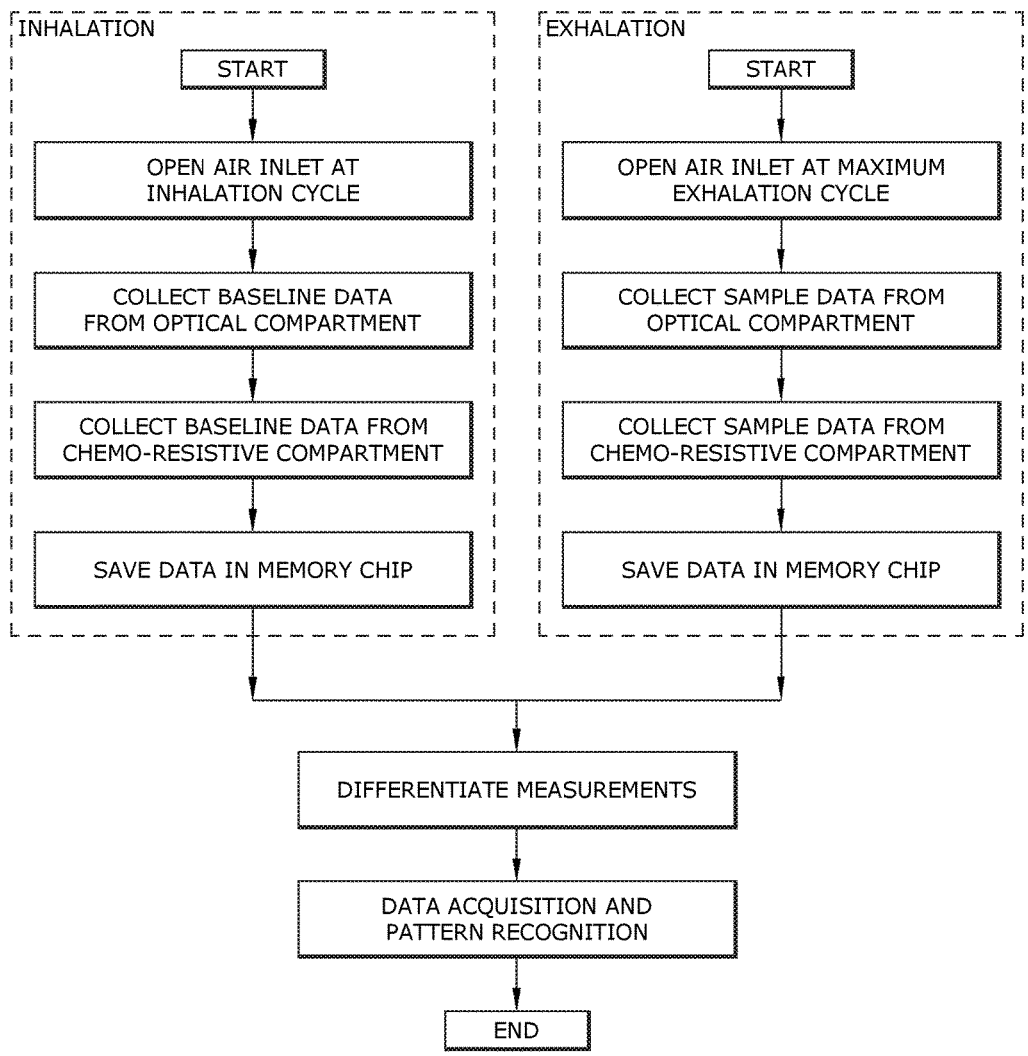
FIG. 4 depicts a flow chart of a method for an optical and chemo-resistive analyses on a breath sample in accordance with certain embodiments of the gas collection apparatus.
Figure 5:
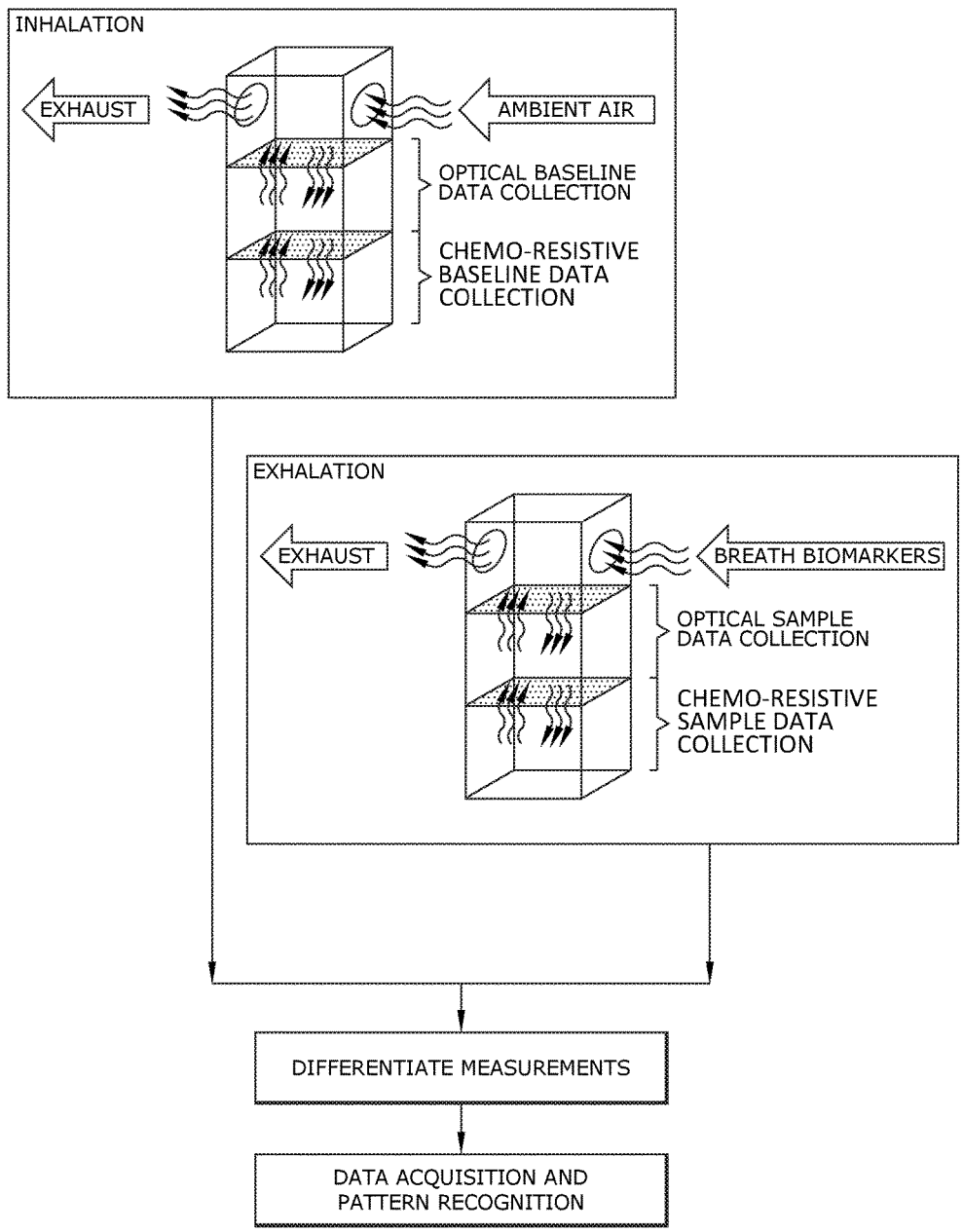
FIG. 5 depicts a schematic view of certain embodiments of the gas collection apparatus.

In certain embodiments, a method for performing an optical and chemo-resistive analyses on a breath sample of a user by using the gas collection apparatus is provided. FIGS. 4-5 depict exemplary steps of certain embodiments of the invention. In one embodiment, the user (not shown)

performs an inhalation cycle at inlet 18. CPU 22 opens both inlet 18 and outlet 20 upon a detection of the inhalation cycle via the inlet sensor. Ambient air is drawn in through outlet 20, flows within housing 44 and out of inlet 18. CPU 22 closes both inlet 18 and outlet 20 to retain the ambient air within housing 44. CPU 22 collects baseline data from the optical based sensor compartment corresponding to a ratio of gases present in the ambient air. Similarly, CPU 22 collects baseline data from the chemo-resistive compartment corresponding to a ratio of gases present in the ambient air. The baseline data generated from completing both optical and chemo-resistive analyses are saved in a memory chip in the gas collection apparatus. In certain embodiments, the ratios of gases present from both analyses are averaged together to generate a more accurate ratio of gases.

The user then performs an exhalation cycle at inlet 18 in the same manner previously described. CPU 22 detects an exhalation cycle via the inlet sensor. In a preferred embodiment, CPU 22 opens both inlet 18 and outlet 20 when the exhalation reaches maximum positive peak pressure 10. At the end of the exhalation's positive peak pressure, CPU automatically closes inlet 18 and outlet 20 to retain breath sample 16 within housing 44. CPU 22 collects sample data from the optical based sensor compartment corresponding to a ratio of gases present in breath sample 16. Similarly, CPU 22 collects sample data from the chemo-resistive compartment corresponding to a ratio of gases present in breath sample 16. The sample data generated by completing both optical and chemo-resistive analyses are saved in a memory chip in the gas collection apparatus. In certain embodiments, the ratios of gases present from both analyses are averaged together to generate a more accurate ratio of gases.

CPU 22 differentiates the measurements corresponding to both the ratio of gases present in the ambient air and the ratio of gases present in breath sample 16. By comparing these ratios, CPU 22 performs a data acquisition and pattern recognition procedure that determines whether breath sample 16 comprises elevated and/or decreased levels of certain gases or elements compared to the ambient air. This data is helpful to the healthcare professional to identify and/or monitor certain conditions and/or diseases suffered by the user.

In certain embodiments, the user may perform several inhalation and exhalation cycles with the gas collection apparatus. The ratios of gases present in all ambient air data are averaged together. Similarly, the ratios of gases present in all breath samples of the user are averaged together. Ultimately, this enhances the accuracy in analyzing the user's breath sample and identifying any corresponding conditions and/or diseases.

It shall be appreciated that the components of the gas collection apparatus described in several embodiments herein may comprise any alternative known materials in the field and be of any color, size and/or dimensions. It shall be appreciated that the components of the gas collection apparatus described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A gas collection apparatus for use by a user to perform optical and chemo-resistive analyses on a breath sample from an exhalation of the user to identify any one of a plurality of conditions suffered by the user, the gas analysis apparatus comprising:
   a housing comprising a sealable inlet and a sealable outlet configured to permit the breath sample to flow therethrough, the housing comprising a first compartment, a second compartment and a third compartment, the second compartment stacked above the first compartment and the third compartment stacked above the second compartment, the third compartment comprising an interior wall coupled thereto that directs the breath sample flowing through the inlet of the housing entirely to the second compartment, the housing configured to permit the breath sample in the second compartment to flow to the first compartment;
   a chemo-resistive analysis assembly comprising a substrate coupled to a sensor array and disposed within the first compartment, the substrate comprising heater elements and being operably connected to a voltage control unit coupled to the housing, the voltage control unit configured to send voltage to the heater elements of the substrate to heat the sensor array to a desired temperature, the chemo-resistive analysis assembly comprising a resistance control unit coupled to the housing and configured to measure resistance in the sensor array;
   an optical analysis assembly comprising a light-emitting diode array and a photodiode array coupled to opposing walls of the second compartment; and
   a processor coupled to the housing and operably connected to the chemo-resistive analysis and optical analysis assemblies;
   wherein the processor is configured to simultaneously perform the chemo-resistive and optical analyses to determine a first ratio of gases present in the breath sample based on the measured resistance in the sensor array upon an interaction with the breath sample in the first compartment and determine a second ratio of gases present in the breath sample based on a change of wavelength of light emitted by the light-emitting diode array as determined by the photodiode array upon an interaction with the breath sample in the second compartment.

2. The gas collection apparatus of claim 1, wherein the processor is operably connected to the sealable inlet and sealable outlet, the processor configured to open the sealable inlet and sealable outlet during the exhalation of the user and close the sealable inlet and sealable outlet at a conclusion of a maximum positive peak pressure of the exhalation of the user to retain the breath sample within the housing.

3. The gas collection apparatus of claim 2, further comprising a first filter membrane dividing the second and third compartments, and a second filter membrane dividing the first and second compartments, wherein each filter membrane of the first and second filter membranes is configured to block moisture or undesirable particulates in the breath sample.

4. The gas collection apparatus of claim 3, further comprising an inlet sensor coupled to the inlet, an outlet sensor coupled to the outlet, and a valve control unit coupled to the housing and operably connected to the processor, inlet sensor and outlet sensor, wherein the valve control unit is configured to open or close the sealable inlet and sealable outlet based on an inhalation or exhalation of the user.

5. A method for performing optical and chemo-resistive analyses on a breath sample from an exhalation of a user to identify any one of a plurality of conditions suffered by the user, the method comprising:

providing an apparatus for collecting gas, the apparatus comprising:
  a housing comprising a sealable inlet and a sealable outlet configured to permit air to flow therethrough, the housing comprising a first compartment, a second compartment and a third compartment, the second compartment stacked above the first compartment and the third compartment stacked above the second compartment, the third compartment comprising an interior wall coupled thereto that directs the breath sample flowing through the inlet of the housing entirely to the second compartment, the housing configured to permit the breath sample in the second compartment to flow to the first compartment;
  a chemo-resistive analysis assembly comprising a substrate coupled to a sensor array and disposed within the first compartment, the substrate comprising heater elements and being operably connected to a voltage control unit coupled to the housing, the voltage control unit configured to send voltage to the heater elements of the substrate to heat the sensor array to a desired temperature, the chemo-resistive analysis assembly comprising a resistance control unit coupled to the housing and configured to measure resistance in the sensor array;
  an optical analysis assembly comprising a light-emitting diode array and a photodiode array coupled to opposing walls of the second compartment; and
  a processor coupled to the housing and operably connected to the chemo-resistive analysis and optical analysis assemblies;
collecting the breath sample within the housing to fill the first and second compartments;
determining a ratio of gases in the breath sample based on the measured resistance in the sensor array upon an interaction with the breath sample in the first compartment, and a change of wavelength of light emitted by the light-emitting diode array as determined by the photodiode array upon an interaction with the breath sample in the second compartment; and
identifying any of the one of a plurality of conditions suffered by the user based on the ratio of gases in the breath sample.

6. The method of claim 5, further comprising collecting an ambient air sample within the housing to fill the first and second compartments; determining a ratio of gases in the ambient air sample based on the measured resistance in the sensor array upon an interaction with the ambient air sample in the first compartment, and a change of wavelength of light emitted by the light-emitting diode array as determined by the photodiode array upon an interaction with the ambient air sample in the second compartment; and comparing the ratios of gases in the breath sample and ambient air sample.

7. The method of claim 6, further comprising identifying the any one of a plurality of conditions suffered by the user based on the ratio of gases in the breath sample and ambient air sample.

* * * * *